United States Patent
Saffitz et al.

(10) Patent No.: US 9,995,756 B2
(45) Date of Patent: Jun. 12, 2018

(54) BUCCAL CELL DIAGNOSIS OF ARRHYTHMOGENIC CARDIOMYOPATHY (ACM)

(71) Applicant: Beth Israel Deaconess Medical Center, Inc., Boston, MA (US)

(72) Inventors: Jeffrey E. Saffitz, Waban, MA (US); Angeliki Asimaki, Boston, MA (US)

(73) Assignee: Beth Israel Deaconess Medical Center, Inc., Boston, MA (US)

( * ) Notice: Subject to any disclaimer, the term of this patent is extended or adjusted under 35 U.S.C. 154(b) by 0 days. days.

(21) Appl. No.: 15/277,609

(22) Filed: Sep. 27, 2016

(65) Prior Publication Data

US 2017/0097363 A1  Apr. 6, 2017

Related U.S. Application Data

(60) Provisional application No. 62/236,006, filed on Oct. 1, 2015.

(51) Int. Cl.
*G01N 33/68* (2006.01)

(52) U.S. Cl.
CPC ... *G01N 33/6893* (2013.01); *G01N 2800/325* (2013.01); *G01N 2800/60* (2013.01)

(58) Field of Classification Search
CPC ......... G01N 33/6893; G01N 2800/325; G01N 2800/60
USPC ..................................................... 514/236.2
See application file for complete search history.

(56) References Cited

U.S. PATENT DOCUMENTS

| | | |
|---|---|---|
| 3,163,160 A | 12/1964 | Cohen |
| 5,738,643 A | 4/1998 | Stredic, III |
| 8,317,728 B2 | 11/2012 | Triva |
| 8,420,385 B2 | 4/2013 | Young et al. |
| 9,011,358 B2 | 4/2015 | Triva |
| 2003/0129738 A1 | 7/2003 | Sorenson et al. |
| 2014/0243706 A1 | 8/2014 | El-Fahmawi |

OTHER PUBLICATIONS

Asimaki et al. "Identification of a new modulator of the intercalated disc in a zebrafish model of arrhythmogenic cardiomyopathy," Sci Transl Med., Jun. 11, 2014; 6(240):240ra74. doi:10.1126/scitranslmed.3008008.
Asimaki et al., "A new diagnostic test for arrhythmogenic right ventricular cardiomyopathy," N Eng J Med, Mar. 12, 2009;360(11):1075-1084.
Basso et al., "Arrhythmogenic right ventricular cardiomyopathy," Lancet, Apr. 11, 2009, 373(9671):1289-1300.
Brockmeyer et al., "Membrane connexin 43 acts as an independent prognostic marker in oral squamous cell carcinoma," Int J Oncol. Jul. 2014;45(1):273-81, Epub Apr. 23, 2014.
Caspi et al., "Modeling of arrhythmogenic right ventricular cardiomyopathy with human induced pluripotent stem cells," Circ Cardiovasc Genet. Dec. 2013;6(6):557-68. Epub Nov. 7, 2013.
Dalai et al., "Arrhythmogenic Right Ventricular Dysplasia," Circulation. Dec. 20, 2005;112(25):3823-32. Epub Dec. 12, 2005.
Delmar and McKenna, "The cardiac desmosome and arrhythmogenic cardiomyopathies: from gene to disease.," Circ Res. Sep. 17, 2010;107(6):700-14.
Fidler et al., "Abnormal connexin43 in arrhythmogenic right ventricular cardiomyopathy caused by plakophilin-2 mutations," J Cell Mol Med, Oct. 2009;13(10):4219-28. Epub Jul. 26, 2008.
Frank et al., "Connexin expression and gap junctional intercellular communication in human squamous cell carcinoma of the head and neck," Otolaryngol Head Neck Surg, Nov. 2006;135(5):736-43.
Garcia-Gras et al., "Suppression of canonical Wnt/beta-catenin signaling by nuclear plakoglobin recapitulates phenotype of arrhythmogenic right ventricular cardiomyopathy," J Clint Invest, Jul. 2006;116(7):2012-21.
Hartzfeld, "Plakophilins: Multifunctional proteins or just regulators of desmosomal adhesion?" Biochim Biophys Acta, Jan. 2007;1773(1):69-77. Epub May 6, 2006.
Kaplan et al., "Remodeling of myocyte gap junctions in arrhythmogenic right ventricular cardiomyopathy due to a deletion in plakoglobin (Naxos disease)," Heart Rhythm. May 2004;1(1):3-11.
Kim et al., "Studying arrhythmogenic right ventricular dysplasia with patient-specific iPSCs," Nature, Feb. 7, 2013;494(7435):105-10. Epub Jan. 27, 2013.
Lodder and Rizzo, "Mouse models in arrhythmogenic right ventricular cardiomyopathy," Front Physiol. Jun. 21, 2012;3:221. eCollection 2012.
Marcus et al., "Right ventricular dysplasia: a report of 24 adult cases," Circulation. Feb.1982;65(2):384-98.
Marcus et al., "Genetics of arrhythmogenic right ventricular cardiomyopathy: a practical guide for physicians," J Am Coll Cardiol, May 14, 2013;61(19):1945-8. Epub Mar. 14, 2013.
Marcus et al., "Diagnosis of arrhythmogenic right ventricular cardiomyopathy/dysplasia: proposed modification of the task force criteria," Circulation, Apr. 6, 2010;121(13):1533-41. Epub Feb. 19, 2010.
McCauley and Wehrens, "Animal models of arrhythmogenic cardiomyopathy," Dis Model Mech, Nov.-Dec. 2009;2(11-12):563-70.
McGrath and Mellerio, "Ectodermal dysplasia-skin fragility syndrome," Dermatol Clin, Jan. 2010;28(1):125-9.
McKoy et al., "Identification of a deletion in plakoglobin in arrhythmogenic right ventricular cardiomyopathy with palmoplantar keratoderma and woolly hair (Naxos disease)," Lancet, Jun. 17, 2000;355(9221):2119-2124.
Neuber et al., "The desmosomal plaque proteins of the plakophilin family," Dermatol Res Pract, 2010;2010:101452. Epub Apr. 21, 2010.
Noorman et al., "Remodeling of the cardiac sodium channel, connexin43, and plakoglobin at the intercalated disk in patients with arrhythmogenic cardiomyopathy," Heart Rhythm, Mar. 2013;10(3):412-9. Epub Nov. 23, 2012.
Pilichou et al., "Arrhythmogenic cardiomyopathy: transgenic animal models provide novel insights into disease pathobiology," Circ Cardiovasc Genet. Jun. 2011;4(3):318-26.

(Continued)

*Primary Examiner* — Kristin A Vajda
(74) *Attorney, Agent, or Firm* — Fish & Richardson P.C.

(57) ABSTRACT

Described herein are, inter alia, methods for diagnosing and treating arrhythmogenic cardiomyopathy (ACM) by detecting cardiac intercalated disk proteins, e.g., desmosomal proteins, mechanical and gap junction proteins, in buccal cells. Exemplary desmosomal and gap junction proteins that can be evaluated in the methods described herein include plakoglobin, plakophilin 1, desmoplakin, and Cx43. The methods can also include selecting and/or administering a treatment for ACM to the subject.

15 Claims, 4 Drawing Sheets
(4 of 4 Drawing Sheet(s) Filed in Color)

(56) References Cited

OTHER PUBLICATIONS

Presland and Dale, "Epithelial structural proteins of the skin and oral cavity: function in health and disease," Crit Rev Oral Biol Med. 2000;11(4):383-408.

Shah et al., "Impact of magnesium sulfate on serum magnesium concentrations and intracellular electrolyte concentrations among patients undergoing radio frequency catheter ablation," Conn Med. May 2008;72(5):261-5.

Tanaka et al., "Novel truncating mutations in PKP1 and DSP cause similar skin phenotypes in two Brazilian families," Br J Dermatol, Mar. 2009; 160(3):692-7. Epub Oct. 21, 2008.

te Riele et al., "Arrhythmogenic right ventricular cardiomyopathy (ARVC): cardiovascular magnetic resonance update," J Cardiovasc Magn Reson, Jul. 20, 2014;16:50, 15 pages.

Thiene et al., "Right ventricular cardiomyopathy and sudden death in young people," N Engl J Med, Jan. 21, 1988;318(3):129-33.

Tsao et al., "Clonal growth of normal human epidermal keratinocytes in a defined medium," J Cell Physiol, Feb. 1982;110(2):219-29.

Wong et al., "Telomere Length of Circulating Leukocyte Subpopulations and Buccal Cells in Patients with Ischemic Heart Failure and Their Offspring," PLoS One, 2011;6(8):e23118. Epub Aug. 18, 2011.

BUCCAL CELL DIAGNOSIS OF ARRHYTHMOGENIC CARDIOMYOPATHY (ACM)

CLAIM OF PRIORITY

This application claims priority under 35 USC § 119(e) to U.S. Patent Application Ser. No. 62/236,006, filed on Oct. 1, 2015. The entire contents of the foregoing are hereby incorporated by reference.

FEDERALLY SPONSORED RESEARCH OR DEVELOPMENT

This invention was made with Government support under Grant No. R01 HL116906 awarded by the National Institutes of Health. The Government has certain rights in the invention.

TECHNICAL FIELD

Described herein are, inter alia, methods for diagnosing and treating arrhythmogenic cardiomyopathy (ACM) by detecting certain cardiac proteins, e.g., intercalated disk proteins such as desmosomal, mechanical and gap junction proteins, in buccal cells. Exemplary desmosomal and gap junction proteins that can be evaluated in the methods described herein include plakoglobin, plakophilin 1, desmoplakin, and Cx43. The methods can also include selecting and/or administering a treatment for ACM to the subject.

BACKGROUND

Arrhythmogenic cardiomyopathy (ACM), also known as arrhythmogenic right ventricular cardiomyopathy in particular (ARVC), is associated with a high frequency of arrhythmias and sudden cardiac death (Marcus et al., Circulation 1982; 65:384-98; Thiene et al., N Engl J Med 1988; 318: 129-33; Dalal et al., Circulation 2005; 112:3823-32). Mutations in genes encoding desmosomal proteins (including desmoplakin, plakoglobin, plakophilin 2, desmocollin 2, and desmoglein 2) have been identified in approximately 60% of patients with ARVC (te Riele et al., J Cardiovasc Magn Reson. 2014; 16:50). However, genetic analysis remains mainly a research tool, and in everyday practice the diagnosis of ACM can be challenging. The clinical presentation may be highly variable, and the genetic penetrance is often low. This is especially true in family members of an index patient in whom establishing a diagnosis of ACM or ARVC requires extensive clinical workup, often leading to equivocal results. Endomyocardial biopsy has not been consistently useful because the structural changes in ARVC tend to spare the subendocardium and do not typically involve the interventricular septum (Thiene et al., 1988, supra) which are the locations in the heart that are typically sampled during conventional endomyocardial biopsy. Thus, the pathological features of ACM/ARVC are often not seen in conventional endomyocardial-biopsy specimens. Moreover, these pathological features tend to be most conspicuous in patients with severe disease and are not well developed in patients with early disease. In the end, the diagnosis usually rests on fulfilling a set of clinical criteria; see, e.g., Marcus et al., Circulation, 2010; 121:1533-1541. Although these criteria are relatively specific, they are not highly sensitive.

SUMMARY

The present inventors have discovered that, surprisingly, buccal mucosa cells (non-cornified squamous epithelial cells lining the inside of the cheek) from subjects with ACM exhibit many of the same changes in immunostaining that are seen in heart tissues. Buccal mucosa cells can be easily and safely obtained, e.g., by simply rubbing the inside of the cheek, e.g., with a swab or scraper; the cells can then be smeared on a slide for subsequent study; larger amounts of cells can also be collected, e.g., using a brush (even a toothbrush) and maintained in tissue culture which allows further analysis in living cells. Thus, the present invention includes methods for the diagnosis of ACM and risk of consequent arrhythmias and sudden cardiac death that include obtaining a sample comprising buccal cells, staining the sample for one or more proteins, e.g., cardiac intercalated disk proteins, and detecting the level, and/or localization of those proteins. Aberrant (i.e., decreased levels or mislocalized) proteins indicate the presence of or risk of developing ACM.

Thus, provided herein are methods for diagnosing arrhythmogenic cardiomyopathy (ACM) in a subject. The methods can include obtaining a sample comprising buccal cells from the subject; detecting the level or localization of one or more desmosomal or gap junction proteins selected from the group consisting of plakoglobin, plakophilin 1, desmoplakin, and Cx43 in the subject sample; comparing the level or localization of the one or more cardiac intercalated disk or desmosomal proteins in the subject sample to a reference level or localization; and diagnosing ACM in the subject when the level in the subject sample is below the reference level, or when the localization differs from the reference localization.

In some embodiments, the reference level is a level in a subject who does not have ACM.

In some embodiments, the reference localization is localization in a subject who does not have ACM, e.g., localization to cellular junctions.

In some embodiments, the buccal cells were obtained by rubbing the inside of the cheek of the subject with a swab, spatula, or scraper.

In some embodiments, the methods include applying the buccal cells onto a surface, e.g., a slide, optionally fixing the cells, e.g., with ethanol, and contacting the cells with an antibody or antigen-binding fragment thereof that binds to a desmosomal protein. In some embodiments, the methods include detecting the level and/or localization of plakoglobin; plakophilin1; desmoplakin; Cx43; plakoglobin and plakophilin1; plakophilin1 and desmoplakin; plakoglobin and desmoplakin; plakophilin1 and Cx43; plakoglobin and Cx43; desmoplakin and Cx43; plakoglobin, plakophilin 1, and Cx43; plakoglobin, desmoplakin, and Cx43; plakoglobin, plakophilin1, and desmoplakin; plakophilin 1, desmoplakin, and Cx43; or plakoglobin, plakophilin 1, desmoplakin, and Cx43.

In some embodiments, the methods include detecting the level and/or localization of plakoglobin and Cx43.

In some embodiments, the methods include contacting the subject sample with antibodies to: plakoglobin; plakophilin1; desmoplakin; Cx43; plakoglobin and plakophilin1; plakophilin1 and desmoplakin; plakoglobin and desmoplakin; plakophilin1 and Cx43; plakoglobin and Cx43; desmoplakin and Cx43; plakoglobin, plakophilin 1, and Cx43; plakoglobin, desmoplakin, and Cx43; plakoglobin, plakophilin1, and desmoplakin; plakophilin 1, desmoplakin, and Cx43; or plakoglobin, plakophilin 1, desmoplakin, and Cx43.

In some embodiments, the methods include contacting the subject sample with antibodies to plakoglobin and Cx43.

In some embodiments, the antibodies are directly or indirectly labeled, and the method comprises detecting the labeled antibodies.

In some embodiments, the subject is at least 7 years of age, e.g., 8, 9, 10, 11, 12, or 13 years of age.

In some embodiments, the methods include selecting a subject diagnosed with ACM for treatment.

In some embodiments, the methods include administering a treatment for ACM to a subject diagnosed with ACM, e.g., a treatment comprising one or more of recommending or advising the subject to avoid strenuous or intense physical activity or exercise; recommending or prescribing or administering one or more Singh Vaughan Williams class II antiarryhthmics (beta blockers) such as propranolol, esmolol, timolol, metoprolol, or atenolol; recommending or prescribing or administering one or more class III antiarrhythmics (K-channel blockers) such as amiodarone, sotalol, ibutilide, dofetilide, dronedarone or E-4031; recommending or performing cardiac ablation; or recommending or implanting an implantable cardiac defibrillator (ICD).

Also provided herein are kits for use in a method described herein. The kits can include one or more of antibodies to: plakoglobin; plakophilin1; desmoplakin; Cx43; plakoglobin and plakophilin1; plakophilin1 and desmoplakin; plakoglobin and desmoplakin; plakophilin1 and Cx43; plakoglobin and Cx43; desmoplakin and Cx43; plakoglobin, plakophilin 1, and Cx43; plakoglobin, desmoplakin, and Cx43; plakoglobin, plakophilin1, and desmoplakin; plakophilin 1, desmoplakin, and Cx43; or plakoglobin, plakophilin 1, desmoplakin, and Cx43, and optionally one or more of: instructions for use in a method described herein; a swab, scraper, or spatula for obtaining buccal cells from a subject; reagents for detecting the antibodies; a slide for receiving the buccal cells; and a fixative reagent for fixing the cells.

In some embodiments, the antibodies are directly or indirectly labeled.

In some embodiments, the fixative reagent comprises ethanol (e.g., 70% to 90% ethanol), methanol, glutaraldehyde, paraformaldehyde, formaldehyde, and/or saponin.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

DESCRIPTION OF DRAWINGS

The patent or application file contains at least one drawing executed in color. Copies of this patent or patent application publication with color drawing(s) will be provided by the Office upon request and payment of the necessary fee.

DETAILED DESCRIPTION

Desmosomes are intercellular junctions that tightly link adjacent cells. ACM is an inherited cardiac disease characterized by fibrofatty replacement of the myocardium, frequent ventricular arrhythmias and a high risk of sudden cardiac death. Over the past decade it has become clear that a large proportion of cases of ACM are associated with mutations in the genes encoding the cardiac desmosome (e.g., PKP2, DSP, JUP, DSC2, DSG2). The cardiac desmosome plays a central role in the mechanical connection of cardiac myocytes. In ACM patients, immunostaining of cardiac myocytes reveals characteristic protein abnormalities including mislocalization of junctional plakoglobin and Cx43 from the cell border to the inside of the cell or to the nucleus.

As previously described, immunohistochemical analysis of a conventional endomyocardial-biopsy sample for levels and localization of certain marker proteins, e.g., cardiac intercalated disk or desmosomal proteins, can be used to detect ACM. However, this still requires cardiac tissue which involves an invasive procedure. While it is reasonable to biopsy the heart of an individual in whom the disease is strongly suspected, it is not feasible to acquire cardiac tissue samples from family members who may carry a possible disease allele but show no evidence of the disease, or from members of the general public to use as a preventive screening measure.

The present inventors have discovered that, surprisingly, buccal mucosa cells (non-cornified squamous epithelial cells lining the inside of the cheek) from subjects with ACM exhibit many of the same changes in immunostaining that are seen in heart tissues. Buccal mucosa cells can be easily and safely obtained, e.g., by simply rubbing the inside of the cheek with a swab or scraper; the cells can then be smeared on a slide for subsequent study. Thus, the present invention includes methods for the diagnosis of ACM and risk of consequent arrhythmias and sudden cardiac death, that include obtaining a sample comprising buccal cells, staining the sample for one or more cardiac intercalated disk proteins, and detecting the presence, level, and/or localization of those proteins. Aberrant (i.e., decreased levels or mislocalized) proteins indicate the presence of or risk of developing ACM.

Alternatively or in addition, larger amounts of buccal cells can also be collected, e.g., using a brush (even a toothbrush) and maintained in tissue culture which allows further analysis in living cells.

Methods of Diagnosis

Included herein are methods for diagnosing, and optionally treating, ACM in a subject. The methods rely on detection of levels and/or subcellular localization of one or a plurality of specific proteins (e.g., cardiac intercalated disk proteins, e.g., cytoskeletal proteins, desmosomal proteins, mechanical and gap junction proteins, and proteins of the degradation complex) associated with ACM in a sample comprising buccal cells; the proteins that can be evaluated in the methods described herein include cardiac intercalated disk or desmosomal proteins plakoglobin, plakophilin 1, desmoplakin, and CX43. These methods can be practiced on any subject, e.g., a subject who has had a cardiac event (such as ventricular arrhythmia or myocardial infarction, e.g., an event that is otherwise unexplained), or a subject who has had a first, second, or third-degree relative who has had a cardiac event (such as ventricular arrhythmia or myocardial infarction, or sudden cardiac death before 35 years of age, e.g., an event that is otherwise unexplained). A subject who has no family history or symptoms can also be screened using the methods described herein. In some embodiments, the subject is at least adolescent or post-pubertal, e.g., is at least 10, 11, 12, 13, 14, 15, 16, 17, 18, 19 or 20 years of age, or is at least 7, 8, or 9 years of age. In some embodiments, the subject is a newborn, or is 1, 2, 3, 4, 5 or 6 years of age.

The methods typically will include obtaining a sample from a subject, and evaluating the subcellular localization and/or level of the desmosomal protein(s) in the sample, and comparing the subcellular localization and/or level with one or more references, e.g., a control reference that represents a normal level or subcellular localization of the desmosomal protein(s), e.g., a level in an unaffected subject, and/or a disease reference that represents a level and/or subcellular localization of the desmosomal protein(s) associated with ACM, e.g., a level or subcellular localization in a subject having ACM.

As used herein the term "sample", when referring to the material to be tested for the presence or subcellular localization of a desmosomal protein(s) using a method described herein, includes buccal cells obtained by swabbing or scraping the cheek of a subject using known methods. In embodiments in which subcellular localization is evaluated, the cells are treated such that they retain their morphology and cytoskeleton substantially intact, though they may be fixed, lysed or permeabilized to permit entrance of antibodies or other labels; suitable methods for fixing the cells include exposing them to one or more of ethanol (e.g., 70% to 90% ethanol), methanol, glutaraldehyde, paraformaldehyde, formaldehyde, and/or saponin. Other methods can be used, so long as the ability to determine subcellular localization of the cardiac intercalated disk or desmosomal proteins is retained if subcellular localization is to be evaluated.

An exemplary method for collection of buccal mucosa samples is as follows. A clean cotton-tipped applicator (Q-tip™) or wood spatula can be used for collection of the specimen. If the mouth is very dry, the applicator or spatula can be moistened (e.g., with saline or sterile water). Usually saliva is sufficient to prevent dehydration. In some cases, the mouth can be rinsed with sterile water before the sample is collected. Material is typically collected from the inside of the cheek by using slight rolling and scraping motions for about 30 seconds on each side. Immediately (e.g., within one minute) after collection, the buccal mucosa sample should be smeared on the center area of each slide (area approximately 2.5×2.5 centimeters). Immediately (e.g., within one minute) after smearing the sample on each slide, the slide can be placed in a beaker containing 70% ethyl alcohol, and left in the alcohol for about 1 minute. The slide should not be allowed to dry before being placed into the alcohol. The slide can then be removed and left at room temperature until the alcohol dries (about 10 minutes). Slides can be stored, e.g., at room temperature in a box with a tight fitting lid.

The level or subcellular localization of a protein can be evaluated using appropriate methods known in the art. The methods typically include revealing labels such as fluorescent, chemiluminescent, radioactive, and enzymatic or dye molecules that provide a signal either directly or indirectly. As used herein, the term "label" refers to the coupling (i.e. physical linkage) of a detectable substance, such as a radioactive agent or fluorophore to an antibody or probe, as well as indirect labeling of the probe or antibody by reactivity with a detectable substance. Examples of detectable substances include, but are not limited to, the following: radioisotopes (e.g., $^{3}H$, $^{14}C$, $^{35}S$, $^{121}I$, $^{131}I$) fluorescent labels, (e.g., FITC, rhodamine, lanthanide phosphors, phycoerythrin (PE) or indocyanine (Cy5)), luminescent labels such as luminol; and enzymatic labels (e.g., horseradish peroxidase, beta-galactosidase, luciferase, alkaline phosphatase, acetylcholinesterase), biotinyl groups (which can be detected by marked avidin e.g., streptavidin containing a fluorescent marker or enzymatic activity that can be detected by optical or calorimetric methods), and predetermined polypeptide epitopes recognized by a secondary reporter (e.g., leucine zipper pair sequences, binding sites for secondary antibodies, metal binding domains, epitope tags). In some embodiments, labels are attached via spacer arms of various lengths to reduce potential steric hindrance. Antibodies may also be coupled to electron dense substances, such as ferritin or colloidal gold, which are readily visualised by electron microscopy.

With regard to subcellular localization of the desmosomal protein(s), a skilled practitioner can determine whether the desmosomal protein(s) are appropriately localized (e.g., at the cell surface or at cell-cell junctions) or mislocalized (e.g., dispersed within the cytoplasm or greatly reduced in cell surface signal intensity). In some embodiments, a method of detecting the desmosomal protein(s) in situ is used on intact cells such that the presence and subcellular localization of the desmosomal protein(s) can be detected. For example, an antibody that binds to a desmosomal protein is labeled with a detectable substance and the desmosomal protein(s) is localized in tissues and cells based upon the presence of the detectable substance. Known cytochemical methods, e.g., using light, fluorescent, or electron microscopy, can be used to determine the subcellular localization of the desmosomal protein(s). In some embodiments, immunohistochemistry (IHC) can be used, e.g., with either direct or indirect labelling. The sample may also be inspected by fluorescent microscopy when immunofluorescence (IF) is performed, as a variation to IHC. Radiography with radioemitting labels can also be used. A skilled practitioner, reviewing the results of such a method (e.g., an image of the cells), can determine whether a desmosomal protein is appropriately localized (e.g., at a cell junction/the cell surface) or mislocalized (e.g., dispersed within the cytoplasm, and/or present at such low levels that it is not visualizable).

Generally speaking, simple visual examination can be used to see if the signal at the cell surface is normal or greatly reduced. As shown in the figures, this is almost always a very clear distinction that does not require complicated measurements of signal intensity, but is immediately apparent upon visualization.

In some embodiments, the level of the protein can be determined in addition to or as an alternative to the subcellular localization of the protein.

In some embodiments, e.g., wherein more than one desmosomal protein is evaluated, the mislocalization of any one of the cardiac intercalated disk or desmosomal proteins evaluated is sufficient to determine that the subject has or is at risk of developing ACM. Mislocalization of certain proteins such as plakophilin1 and desmoplakin may also predict which genes may be mutated in patients with ACM. In some embodiments, a score is calculated in which the mislocalization of the desmosomal protein(s) is quantified; see, e.g., the Subcellular Localization Index described in US20150094224.

In some embodiments, standard electrophoretic and quantitative immunoassay methods can be used for determining levels of proteins, including (but not limited to), Western blot; enzyme linked immunosorbent assay (ELISA); biotin/avidin type assays; protein array detection; radio-immunoassay; immunohistochemistry (IHC); immune-precipitation assay; FACS (fluorescent activated cell sorting); mass spectrometry (Kim (2010) Am J Clin Pathol 134:157-162; Yasun (2012) Anal Chem 84(14):6008-6015; Brody (2010) Expert Rev Mol Diagn 10(8):1013-1022; Philips (2014) PLOS One 9(3):e90226; Pfaffe (2011) Clin Chem 57(5): 675-687). For example, an ELISA method may be used to determine the levels of a protein, wherein the wells of a mictrotiter plate are coated with an antibody against which the protein is to be tested. The sample containing or suspected of containing the biological marker is then applied to the wells. After a sufficient amount of time, during which antibody-antigen complexes would have formed, the plate is washed to remove any unbound moieties, and a detectably labelled molecule is added. Again, after a sufficient period of incubation, the plate is washed to remove any excess, unbound molecules, and the presence of the labeled molecule is determined using methods known in the art. Variations of the ELISA method, such as the competitive ELISA or competition assay, and sandwich ELISA, may also be used, as these are well-known to those skilled in the art.

Mass spectrometry, and particularly matrix-assisted laser desorption/ionization mass spectrometry (MALDI-MS) and surface-enhanced laser desorption/ionization mass spectrometry (SELDI-MS), is also useful for the detection of levels of the proteins. (See U.S. Pat. Nos. 5,118,937; 5,045,694; 5,719,060; 6,225,047)

In some embodiments, where the subcellular localization and/or level of the desmosomal protein(s) is comparable to the subcellular localization and/or level of the desmosomal protein(s) in the disease reference, and the subject optionally has one or more symptoms associated with ACM, then the subject is diagnosed with (and optionally treated for) ACM. In some embodiments, the subject has no overt signs or symptoms of ACM, but the subcellular localization and/or level of the desmosomal protein(s) evaluated is comparable to the subcellular localization and/or level of the desmosomal protein(s) in the disease reference, then the subject has ACM or has an increased risk of developing ACM (i.e., an increased risk as compared to a subject who has normal subcellular localization and/or level of the desmosomal protein(s)). In some embodiments, once it has been determined that a person has ACM, or has an increased risk of developing ACM, then a treatment, e.g., as known in the art or as described herein, can be administered.

Suitable reference values can be determined using methods known in the art, e.g., using standard clinical trial methodology and statistical analysis. The reference values can have any relevant form. In some cases, the reference comprises a predetermined value for a meaningful level of the desmosomal protein(s), e.g., a control reference level that represents a normal level of the desmosomal protein(s), e.g., a level in an unaffected subject or a subject who is not at risk of developing ACM, and/or a disease reference that represents a level of the proteins associated with ACM, e.g., a level in a subject having ACM.

The predetermined level can be a single cut-off (threshold) value, such as a median or mean, or a level that defines the boundaries of an upper or lower quartile, tertile, or other segment of a clinical trial population that is determined to be statistically different from the other segments. It can be a range of cut-off (or threshold) values, such as a confidence interval. It can be established based upon comparative groups, such as where association with risk of developing disease or presence of disease in one defined group is a fold higher, or lower, (e.g., approximately 2-fold, 4-fold, 8-fold, 16-fold or more) than the risk or presence of disease in another defined group. It can be a range, for example, where a population of subjects (e.g., control subjects) is divided equally (or unequally) into groups, such as a low-risk group, a medium-risk group and a high-risk group, or into quartiles, the lowest quartile being subjects with the lowest risk and the highest quartile being subjects with the highest risk, or into n-quantiles (i.e., n regularly spaced intervals) the lowest of the n-quantiles being subjects with the lowest risk and the highest of the n-quantiles being subjects with the highest risk.

Subjects associated with predetermined values are typically referred to as reference subjects. For example, in some embodiments, a control reference subject does not have a disorder described herein (e.g., ACM). In some cases it may be desirable that the control subject is a first degree relative of a subject with ACM, and in other cases it may be desirable that a control subject is unrelated. In some cases it may be desirable that the control subject has ACM and in other cases it may be desirable that a control subject does not have ACM.

A disease reference subject is one who has (or has an increased risk of developing) one or more of ACM. An increased risk is defined as a risk above the risk of subjects in the general population.

Thus, in some cases the level of the desmosomal protein(s) in a subject being less than or equal to a reference level of the desmosomal protein(s) is indicative of a clinical status, e.g., indicative of a disorder as described herein, e.g., ACM. In other cases the level of the desmosomal protein(s) in a subject being greater than or equal to the reference level of the desmosomal protein(s) is indicative of the absence of disease or normal risk of the disease. In some embodiments, the amount by which the level in the subject is the less than the reference level is sufficient to distinguish a subject from a control subject, and optionally is a statistically significantly less than the level in a control subject. In cases where the level of the desmosomal protein(s) in a subject being equal to the reference level of the desmosomal protein(s), the "being equal" refers to being approximately equal (e.g., not statistically different).

The predetermined value can depend upon the particular population of subjects (e.g., human subjects) selected. For example, an apparently healthy population will have a different 'normal' range of levels of the desmosomal protein(s) than will a population of subjects which have, are likely to have, or are at greater risk to have, a disorder described herein. Accordingly, the predetermined values selected may take into account the category (e.g., sex, age, health, risk, presence of other diseases) in which a subject (e.g., human subject) falls. Appropriate ranges and categories can be selected with no more than routine experimentation by those of ordinary skill in the art. In characterizing likelihood, or risk, numerous predetermined values can be established.

In some embodiments, e.g., wherein more than one desmosomal protein is evaluated, a decreased level (level below a reference) of any one of the cardiac intercalated disk or desmosomal proteins evaluated is sufficient to determine that the subject has or is at risk of developing ACM.

The cardiac intercalated disk or desmosomal proteins that can be evaluated in the methods described herein include plakoglobin, plakophilin 1, desmoplakin, and Cx43. Antibodies that bind to these proteins, or antigen-binding fragments thereof, can be obtained commercially or using methods known in the art. In preferred embodiments, the antibodies bind specifically to the cardiac intercalated disk or desmosomal proteins and do not cross-react with other proteins, e.g., PKP1 antibodies do not bind to PKP2.

JUP—Plakoglobin

Junctional plakoglobin is a major cytoplasmic protein present in submembranous plaques of both desmosomes and intermediate junctions. Plakoglobin complexes with cadherins and desmosomal cadherins and is a member of the catenin family.

A number of splice variants exist; some human plakoglobin transcript sequences are in Genbank at NM_002230.2 (variant 1) and NM_021991.2 (variant 2); both variants encode the same protein, NP_068831.1 and NP_002221.1. The RefSeqGene accession number for the human JUP gene is NG_009090.2.

PKP1—Plakophilin 1

Plakophilin proteins normally localize to desmosomes of stratified, complex, and transitional epithelia; the proteins participate in linking cadherins to intermediate filaments in the cytoskeleton and may play a role in molecular recruitment and stabilization during desmosome formation. PKP1 is not typically believed to be expressed in the heart and subjects with skin abnormalities related to PKP1 mutations have no cardiac disease or pathology (Tanaka et al., British Journal of Dermatology 2009 160:692-697; McGrath and Mellerio, Dermatol Clin. 2010, 28(1):125-9; Neuber et al., Dermatol Res Pract. 2010, 2010:101452).

Two human transcript variants encoding different isoforms have been described for this gene, in GenBank at NM_000299.3 (variant 1b) encoding NP_000290.2, the longer isoform 1b, and NM_000299.3 (variant 1a), encoding NP_000290.2, the shorter plakophilin-1 isoform 1b. The RefSeqGene accession number for the human PKP1 gene is NG_023337.1.

DSP—Desmoplakin

Desmoplakin is an essential component of functional desmosomes that anchors intermediate filaments to desmosomal plaques, and mutations in the DSP gene are associated with several cardiomyopathies and keratodermas as well as paraneoplastic pemphigus.

Two isoforms have been described. See GenBank Acc. No. NM_004415.2 (variant 1), which encodes NP_004406.2 (desmoplakin isoform I), and NM_001008844.1 (variant 2), which encodes NP_001008844.1 (desmoplakin isoform II).

The RefSeqGene accession number for the human DSP gene is NG_008803.1.

Cx43—a.k.a. GJA1, Gap Junction Protein, Alpha 1, 43 kDa

The Cx43 protein is the major protein of cardiac gap junctions that synchronize contraction of the heart. Mutations in the GJA1 gene are associated with heart malformations, and redistribution of Cx43 has been described in ACM (see Asimaki et al, NEJM, 2009; 360:1075-1084).

The human Cx43 transcript is in GenBank at NM_000165.4, and the protein sequence is at NP_000156.1. The RefSeqGene accession number for the human GJA1 gene is NG_008308.1.

Methods of Treatment

In some embodiments, the methods described herein further include selecting and/or administering a treatment to a subject identified by a method described herein as having or being at risk for ACM. The methods can include recommending or advising the subject to avoid strenuous or intense physical activity or exercise; recommending or prescribing or administering one or more Singh Vaughan Williams class II antiarryhthmics (beta blockers) such as propranolol, esmolol, timolol, metoprolol, or atenolol; recommending or prescribing or administering one or more class III anti-arrhythmics (K-channel blockers) such as amiodarone, sotalol, ibutilide, dofetilide, dronedarone or E-4031; recommending or performing cardiac ablation; or recommending or implanting an implantable cardiac defibrillator (ICD).

Test/Assay Kits

Also provided for herein are test or assay kits that can be used in the methods described herein. For example, the kit can include one or more compounds or agents capable of detecting a desmosomal protein in a sample (e.g., antibodies or antigen-binding fragments thereof, preferably directly or indirectly labeled), and optionally one or more standards or controls. The compound or agent can be packaged in a suitable container. The kit can further comprise instructions for using the kit to detect cardiac intercalated disk or desmosomal proteins in a method described herein; a swab, scraper, or spatula for obtaining buccal cells from a subject; reagents for detecting the antibodies; a slide or slides for receiving the buccal cells; and a fixative reagent for fixing the cells. Suitable swabs, scrapers, or spatulas are known in the art, including standard cotton swabs and wooden or rubber scrapers, as well as collection systems for buccal cells; see also U.S. Pat. No. 5,738,643; US 20140243706; U.S. Pat. No. 8,317,728; U.S. Pat. No. 8,420,385; U.S. Pat. No. 9,011,358; US20030129738; and U.S. Pat. No. 3,163,160.

Methods of Screening

As described herein, larger amounts of buccal cells can also be collected, e.g., using a brush (even a toothbrush) and maintained in tissue culture (e.g., in the presence of a medium for growth of normal human keratinocytes, e.g., KGM-CD (Lonza) or Stemline™ Keratinocyte Basal Medium (Sigma-Aldrich) optionally supplemented with insulin and/or growth factors, see also Tsao et al., Journal of Cellular Physiology 110(2):219-229 (1982)). These cultured buccal cells can be used, e.g., in drug screens designed to determine if a particular drug is able to reverse the pathological changes seen in buccal mucosa cells in patients with ACM. In these methods, a test compound is applied to the cells and levels and/or localization of the cardiac intercalated disk or desmosomal proteins plakoglobin, plakophilin 1, desmoplakin, and/or CX43 are evaluated. A test compound that is able to restore levels and/or localization of the proteins to normal or near normal is selected as a candidate compound for the treatment of ACM.

Thus, included herein are methods for screening test compounds, e.g., polypeptides, polynucleotides, inorganic or organic large or small molecule test compounds, to identify agents useful in the treatment of ACM.

As used herein, "small molecules" refers to small organic or inorganic molecules of molecular weight below about 3,000 Daltons. In general, small molecules useful for the invention have a molecular weight of less than 3,000 Daltons (Da). The small molecules can be, e.g., from at least about 100 Da to about 3,000 Da (e.g., between about 100 to about 3,000 Da, about 100 to about 2500 Da, about 100 to about 2,000 Da, about 100 to about 1,750 Da, about 100 to about 1,500 Da, about 100 to about 1,250 Da, about 100 to about 1,000 Da, about 100 to about 750 Da, about 100 to about 500 Da, about 200 to about 1500, about 500 to about 1000, about 300 to about 1000 Da, or about 100 to about 250 Da).

The test compounds can be, e.g., natural products or members of a combinatorial chemistry library. A set of diverse molecules should be used to cover a variety of functions such as charge, aromaticity, hydrogen bonding, flexibility, size, length of side chain, hydrophobicity, and rigidity. Combinatorial techniques suitable for synthesizing small molecules are known in the art, e.g., as exemplified by Obrecht and Villalgordo, *Solid-Supported Combinatorial and Parallel Synthesis of Small-Molecular-Weight Compound Libraries*, Pergamon-Elsevier Science Limited (1998), and include those such as the "split and pool" or "parallel" synthesis techniques, solid-phase and solution-phase techniques, and encoding techniques (see, for example, Czarnik, Curr. Opin. Chem. Bio. 1:60-6 (1997)). In addition, a number of small molecule libraries are commercially available. A number of suitable small molecule test compounds are listed in U.S. Pat. No. 6,503,713, incorporated herein by reference in its entirety.

Libraries screened using the methods of the present invention can comprise a variety of types of test compounds. A given library can comprise a set of structurally related or unrelated test compounds. In some embodiments, the test compounds are peptide or peptidomimetic molecules. In some embodiments, the test compounds are nucleic acids.

In some embodiments, the test compounds and libraries thereof can be obtained by systematically altering the structure of a first test compound, e.g., a first test compound that is structurally similar to a known natural binding partner of the target polypeptide, or a first small molecule identified as capable of binding the target polypeptide, e.g., using methods known in the art or the methods described herein, and correlating that structure to a resulting biological activity, e.g., a structure-activity relationship study. As one of skill in the art will appreciate, there are a variety of standard methods for creating such a structure-activity relationship. Thus, in some instances, the work may be largely empirical, and in others, the three-dimensional structure of an endogenous polypeptide or portion thereof can be used as a starting point for the rational design of a small molecule compound or compounds. For example, in one embodiment, a general library of small molecules is screened, e.g., using the methods described herein.

In some embodiments, a test compound is applied to a test sample, e.g., a cell or living tissue or organ, e.g., an eye, and one or more effects of the test compound is evaluated. In a cultured or primary cell for example, the ability of the test compound to normalize (i.e., return to normal or near-normal, at least 60% of normal, e.g., 60%, 70%, 80%, 90%, or 95% of normal) levels and/or localization of the cardiac intercalated disk or desmosomal proteins plakoglobin, plakophilin 1, desmoplakin, and/or CX43 is evaluated.

In some embodiments, the test sample is, or is derived from (e.g., a sample taken from) an in vivo model of ACM. For example, an animal model, e.g., a rodent such as a mouse, that has a mutation associated with ACM can be used. A number of animal models of ACM are known in the art; see, e.g., McCauley and Wehrens, Dis Model Mech. 2009 November-December; 2(11-12):563-70; Pilichou et al., Circ Cardiovasc Genet. 2011 June; 4(3):318-26; Lodder and Rizzo. Front. Physio. 3:221. doi: 10.3389/fphys.2012.00221 (2012); Delmar and McKenna, Circulation Research. 107:700-714 (2010).

Alternatively, the test sample can be from a human subject who has ACM, has a mutation associated with ACM, or an unaffected relative, e.g., a first degree relative, thereof. In some embodiments an unaffected relative, e.g., a first degree relative, of a human who has ACM is used as a control; the relative may or may not have a mutation associated with ACM.

Methods for evaluating each of these effects are known in the art. For example, ability to modulate expression of a protein can be evaluated at the gene or protein level, e.g., using quantitative PCR or immunoassay methods. In some embodiments, high throughput methods, e.g., protein or gene chips as are known in the art (see, e.g., Ch. 12, Genomics, in Griffiths et al., Eds. *Modern genetic Analysis*, 1999, W. H. Freeman and Company; Ekins and Chu, Trends in Biotechnology, 1999, 17:217-218; MacBeath and Schreiber, Science 2000, 289(5485):1760-1763; Simpson, *Proteins and Proteomics: A Laboratory Manual*, Cold Spring Harbor Laboratory Press; 2002; Hardiman, *Microarrays Methods and Applications: Nuts & Bolts*, DNA Press, 2003), can be used to detect an effect on protein levels. Ability to modulate protein localization and levels can be evaluated, e.g., using imaging methods such as fluorescence microscopy.

A test compound that has been screened by a method described herein and determined to normalize levels and/or localization of the cardiac intercalated disk or desmosomal proteins plakoglobin, plakophilin 1, desmoplakin, and/or CX43 can be considered a candidate compound. A candidate compound that has been screened, e.g., in an in vivo model of a disorder, e.g., an animal model with an ACM mutation, and determined to have a desirable effect on the disorder, e.g., on one or more symptoms of the disorder, can be considered a candidate therapeutic agent. Candidate therapeutic agents, once screened in a clinical setting, are therapeutic agents. Candidate compounds, candidate therapeutic agents, and therapeutic agents can be optionally optimized and/or derivatized, and formulated with physiologically acceptable excipients to form pharmaceutical compositions.

Thus, test compounds identified as "hits" (e.g., test compounds that normalize levels and/or localization of the cardiac intercalated disk or desmosomal proteins plakoglobin, plakophilin 1, desmoplakin, and/or CX43) in a first screen can be selected and systematically altered, e.g., using rational design, to optimize binding affinity, avidity, specificity, or other parameter. Such optimization can also be screened for using the methods described herein. Thus, in one embodiment, the invention includes screening a first library of compounds using a method known in the art and/or described herein, identifying one or more hits in that library, subjecting those hits to systematic structural alteration to create a second library of compounds structurally related to the hit, and screening the second library using the methods described herein.

Test compounds identified as hits can be considered candidate therapeutic compounds, useful in treating ACM. A variety of techniques useful for determining the structures of "hits" can be used in the methods described herein, e.g., NMR, mass spectrometry, gas chromatography equipped with electron capture detectors, fluorescence and absorption spectroscopy. Thus, the invention also includes compounds identified as "hits" by the methods described herein, and methods for their administration and use in the treatment, prevention, or delay of development or progression of a disorder described herein.

Test compounds identified as candidate therapeutic compounds can be further screened by administration to an animal model of ACM, as known in the art. The animal can be monitored for a change in the disorder, e.g., for an improvement in a parameter of the disorder, e.g., a parameter related to clinical outcome. In some embodiments, the parameter is arrhythmia, e.g., ventricular tachyarrhythmia, and an improvement would be a decrease in frequency or cessation of arrhythmias. In some embodiments, the subject is a human, e.g., a human with ACM and an implantable cardioverter-defibrillator device, and the parameter is a decrease in activation of the device.

EXAMPLES

The invention is further described in the following examples, which do not limit the scope of the invention described in the claims.

Example 1

Characterizing the Molecular Pathology of Arrhythmogenic Cardiomyopathy in Buccal Mucosa Cells To find a surrogate tissue for the heart that can be studied in ACM probands and family members, buccal mucosa cells, which can be easily and safely obtained from large numbers of subjects at minimal cost, were investigated. As shown herein, surprisingly, buccal mucosa cells from ACM patients exhibited many features previously documented in cardiac myocytes.

Materials and Methods

The following materials and methods were used in the Examples.

Patients, Family Members, Controls:

Buccal mucosa samples were obtained from a total of 103 subjects categorized into 4 groups. Group 1 consisted of 40 patients who fulfilled international task force criteria for the diagnosis of ACM[11] and who had a documented mutation in a desmosomal gene. Group 2 included 40 healthy individuals with no history of heart disease who served as controls. Group 3 consisted of 16 family members (some related to patients in Group 1) who were known to carry a disease allele but showed no evidence of heart disease. Group 4 consisted of 7 patients with other types of heart diseases including hypertrophic cardiomyopathy (HCM, n=4), dilated cardiomyopathy (DCM; n=2) and ischemic heart disease (n=1). All subjects provided written informed consent, and sample collection protocols were approved by appropriate institutional review boards. Standard HIPAA protocols were followed, and database information was stored in password-encrypted files. All buccal mucosa samples were coded and analyzed in a blinded fashion.

Buccal mucosa smears were prepared from each subject. In most cases, enough smears were prepared to allow immunostaining for multiple proteins, but in a few cases only a limited number of smears were available. In selected cases, additional samples were obtained for preparation of buccal mucosal cell cultures.

Buccal Mucosa Sampling and Preparation of Smears:

A clean cotton-tipped swab (Q-tip) was used for collection of the specimen. Material was collected from the inside of the cheek by using slight rolling and scraping motions for about 30 seconds on each side. Immediately after collection, the buccal mucosa material was smeared on the center area of microscope slides (2.5×2.5 centimeters), which were subsequently dipped in 70% ethanol for ~1 minute to fix the sample. The slides were allowed to air dry and stored at room temperature before being immunostained.

Buccal Mucosa Culture Protocol:

The oral cavity was first rinsed thoroughly with antiseptic mouthwash. Buccal mucosa cells were collected with a sterile toothbrush which was lightly scraped on the inside of both cheeks for ~2 minutes. The oral cavity was washed with 15 ml of sterile saline which was collected in a centrifuge tube. The toothbrush itself was washed in an additional 10 ml of saline. The same process was repeated one or more times. The resultant cell suspension was centrifuged at 3000 g for 5 minutes. The pellet was washed once in sterile PBS, re-centrifuged and subsequently re-suspended in 20 ml of PBS supplemented with 5% penicillin/streptomycin and 7 mM fungizone for 30 minutes. The cells were then washed twice in PBS, reconstituted in KGM™-CD chemically defined keratinocyte growth medium (LONZA) and seeded on matrigel-coated chamber slides, where they were maintained at 37° C., 5% $CO_2$ for up to 7 days. Selected cultures were incubated with SB216763 (5 mM) for 24 hours prior to immunostaining.

Immunohistochemistry:

Buccal mucosa smears were immunostained using established protocols.[3,8] Cells were simultaneously blocked and permeabelized for 45 minutes in 3% normal goat serum, 1% w/v BSA, and 0.15% Triton X-100 in PBS, followed by an overnight incubation at 4° C. with one of the following primary antibodies: mouse monoclonal anti-plakoglobin (Sigma), mouse monoclonal anti-plakophilin-1 (Santa Cruz Biotechnology), mouse monoclonal anti-desmoplakin (Fitzgerald) or rabbit polyclonal anti-Cx43 (AbCam) antibodies. Slides were then incubated with Cy3-conjugated secondary antibodies (Jackson ImmnunoResearch) for 2 hours at room temperature and counterstained with DAPI.

Buccal mucosa cultures were washed in PBS, fixed in 4% paraformaldehyde and, after being washed 3 additional times in PBS, were immunostained as described above with mouse monoclonal anti-plakoglobin (Sigma) or mouse monoclonal anti-Cx43 (Millipore) primary antibodies. All immunostained preparations were imaged at 40× using a ZEISS inverted confocal microscope.

Statistical Analysis:

Data were reported as frequency counts (%) for categorical variables, which were compared between groups with Chi-square or Fisher's exact test using SPSS 21.0 software. $p<0.05$ was considered significant.

Example 1.1

Immunohistochemical Analysis of Expression of Cell-Cell Junction Proteins in Normal Buccal Mucosa Cells Before characterizing expression of cell-cell junction proteins in buccal mucosa cells in ACM patients, we optimized immunostaining conditions in cells from normal subjects. For each primary antibody, we determined the minimal concentration (i.e., maximum antibody dilution) that still led to bright immunofluorescent signal in normal cells. This essential step was designed to optimally demonstrate any potential reduction in signal intensity in ACM patient cells. Once suitable primary antibody dilutions had been determined in a pilot study of normal cells, we used these conditions throughout the study.

Figure 1:
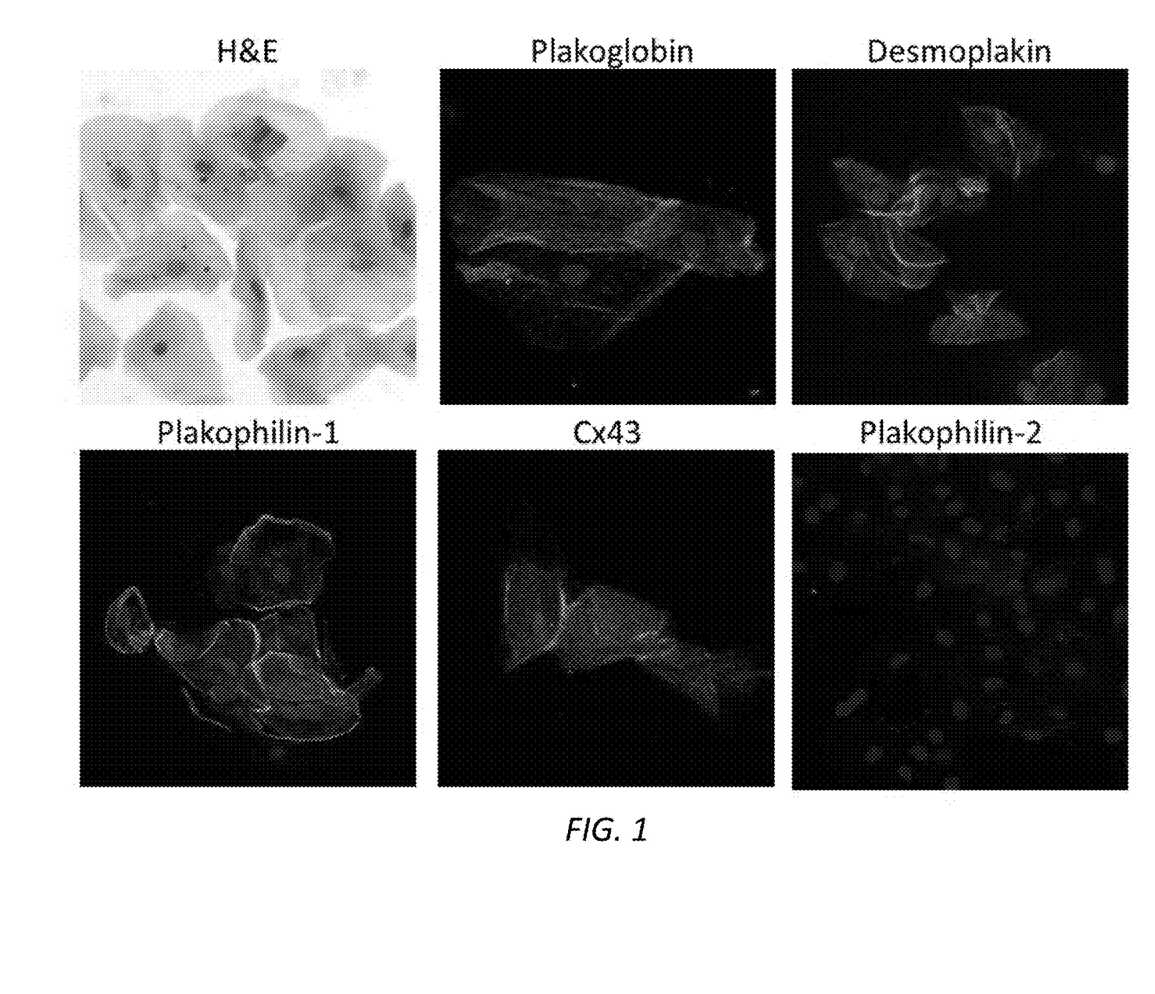
FIG. 1: Representative images of normal buccal mucosa smears. Cells stained with hematoxylin and eosin (H&E) show typical squamous morphology with central nuclei and clearly delineated cell borders. Buccal mucosa cells immunostained with antibodies against desmosomal and gap junction proteins show strong immunoreactive signals for plakoglobin, desmoplakin, plakophilin-1 and Cx43 concentrated at the edges of the cells. No apparent signal is seen for plakophilin-2 which is expressed in the heart but not in epithelial tissues. Cell nuclei (blue) are stained with DAPI.

As shown in representative images in FIG. 1, buccal smears consisted of flattened squamous cells with small central nuclei and clearly identified edges. The immunostaining protocol resulted in abundant fluorescent signal in normal cells for the desmosomal proteins plakoglobin, desmoplakin and plakophilin-1, and the gap junction protein Cx43. Signal for each of these proteins was present at the cell surface and, depending on the protein being studied, was also seen within the cell. No signal was detected in buccal mucosa cells stained for plakophilin-2, the plakophilin expressed in cardiac myocytes.

Example 1.2

Expression of Cell-Cell Junction Proteins in Buccal Mucosa Cells from ACM Patients with Desmosomal Mutations To determine whether changes in cell-cell junction proteins occur in buccal mucosa cells in ACM, we tested samples from patients with clinically documented ACM and a known mutation in a desmosomal gene (Group 1). This included patients with autosomal dominant mutations in PKP2 (n=26), DSG2 (n=4), DSC2 (n=2), and DSP (n=2); and 6 patients with a recessive mutation in JUP that causes the cardiocutaneous syndrome Naxos disease' (total n=40). We immunostained these samples for plakoglobin and Cx43 which almost always show reduced junctional signal in the hearts of patients with ACM.[3] As shown in Table 1 and in representative images in FIG. 2, signal for plakoglobin was depressed or absent in 21 of 26 patients with PKP2 mutations and in all 14 patients with other desmosomal mutations. Signal for Cx43 was reduced in 32 of 33 patient samples (additional smears for Cx43 staining were not available in 7 patients) (Table 1 and FIG. 2). The only case with apparently normal Cx43 staining was a Naxos disease patient in whom plakoglobin signal was depressed. Group 1 ACM patient samples were compared to 40 control samples (Group 2) including 11 from the island of Naxos where patients with the recessive mutation in JUP originated. Strong signals for plakoglobin and Cx43 were seen in all 40 controls (Table 1, FIGS. 1 and 2).

TABLE 1

Summary of immunohistochemical findings in buccal mucosa smears in 4 groups of subjects (*p < 0.001 vs. controls; #p < 0.001 vs. patients with other heart diseases).

|   |   | Depressed plakoglobin signal | Depressed Cx43 signal | Depressed plakophilin-1 signal | Depressed desmoplakin signal |
|---|---|---|---|---|---|
| GROUP 1 | ACM patients (n = 40) | | | | |
|   | PKP2 (n = 26) | 21/26 | 16/20 | 20/20 | 0/20 |
|   | DSG2 (n = 4) | 4/4 | 2/2 | 0/2 | 2/2 |
|   | DSC2 (n = 2) | 2/2 | 2/2 | 0/2 | 2/2 |
|   | DSP (n = 2) | 2/2 | 2/2 | 0/2 | 2/2 |
|   | JUP (n = 6) | 6/6 | 5/6 | 0/6 | 0/6 |
|   |   | Total: 35/40*# | Total: 27/32* | Total: 20/32 | Total: 6/32 |
| GROUP 2 | Controls (n = 40) | Total: 0/40 | Total: 0/39 | Total: 0/39 | Total: 0/39 |
| GROUP 3 | Unaffected carriers (n = 16) | | | | |
|   | 2157del2 JUP (n = 12) | 10/12 | 11/12 | 0/11 | 0/11 |
|   | DSC2 (n = 1) | 1/1 | 1/1 | 0/1 | 1/1 |
|   | DSP (n = 1) | 1/2 | 2/2 | 0/2 | 2/2 |
|   | PKP2 (n = 1) | 1/1 | 1/1 | 1/1 | 0/1 |
|   |   | Total: 13/16* | Total: 15/16* | Total: 1/15 | Total: 3/15 |
| GROUP 4 | Patients with other CMs (n = 7) | | | | |
|   | HCM (n = 4) | 0/4 | 4/4 | | |
|   | DCM (n = 2) | 0/2 | 2/2 | | |
|   | Ischemia (n = 1) | 0/1 | 1/1 | | |
|   |   | Total: 0/7 | Total: 7/7* | | |

As previously reported, intercalated disc signals for other desmosomal proteins including plakophilin-2 and desmoplakin are reduced in the hearts of some but not all patients with ACM.[3] To determine whether signals for plakophilin and desmoplakin are altered in buccal mucosa cells from ACM patients, samples were immunostained with antibodies against plakophilin-1 and desmoplakin. As shown in Table 1 and in representative images in FIG. 2, signal for plakophilin-1 was depressed in all ACM patients with PKP2 mutations in whom smears were available for study (n=20), but in none of 12 ACM patients with mutations in other desmosomal genes including autosomal dominant mutations in DSG2 (n=2), DSC2 (n=2) or DSP (n=2), and the recessive mutation in JUP (n=6). Additional smears for plakophilin-1 staining were available in 4 of 5 patients with PKP2 mutations who showed normal plakoglobin signal (see Table 1) and in all 4 cases, signal for plakophilin-1 was virtually absent.

Figure 2:
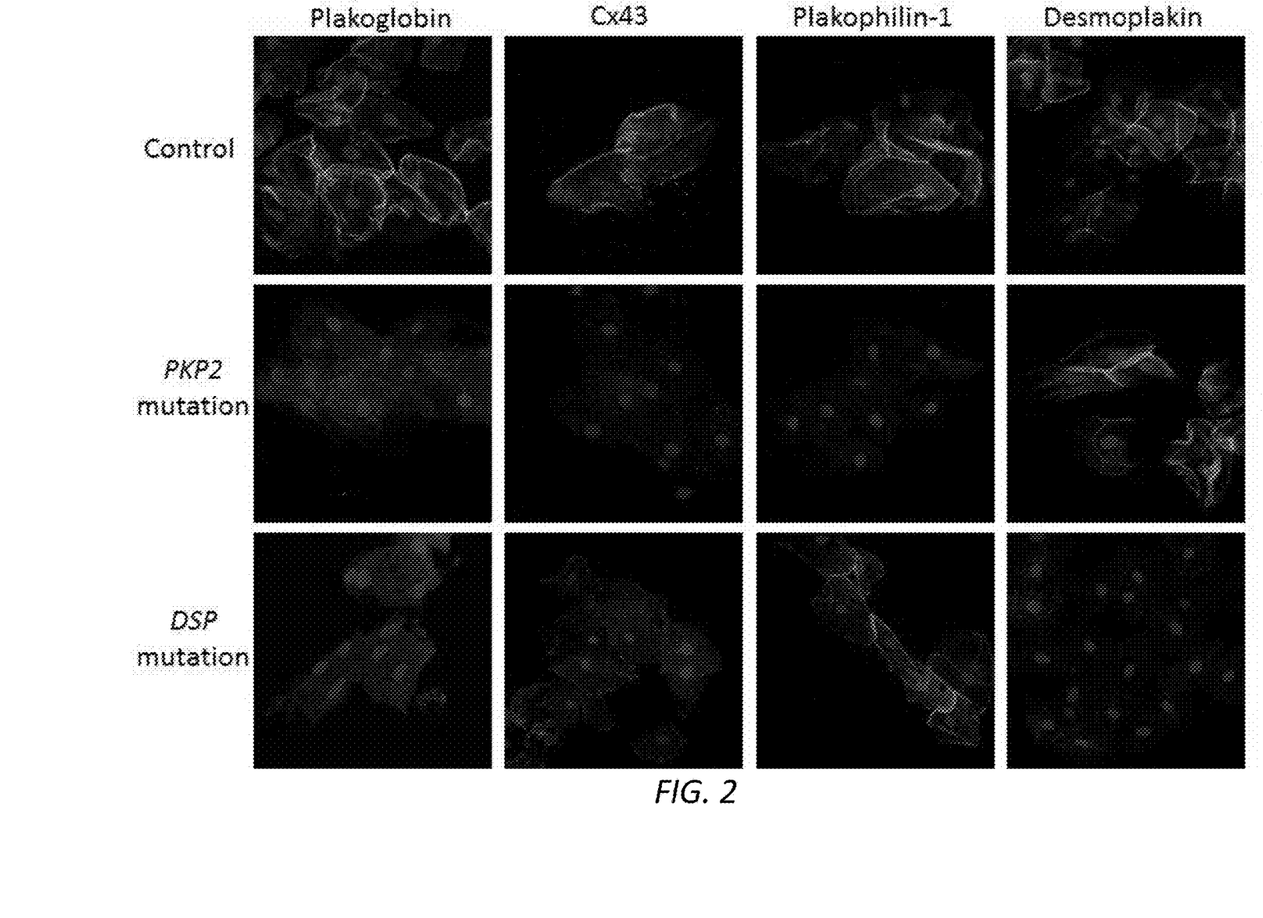
FIG. 2: Representative images of buccal mucosa smears from a control, and ACM patients with mutations in PKP2 or DSP. Both patients show loss of junctional signal for plakoglobin and Cx43 compared to controls. Cells from the patient with a PKP2 mutation show loss of signal for plakophilin-1 but not desmoplakin, whereas cells from the patient with a DSP mutation show loss of signal for desmoplakin but not plakophilin-1. Cell nuclei (blue) are stained with DAPI.

Signal for desmoplakin was reduced in ACM patients with mutations in DSP (n=2), DSC2 (n=2) or DSG2 (n=2) but not in patients with mutations in PKP2 (n=20) or JUP (n=6) (Table 1, FIG. 2).

Example 1.3

Expression of Cell-Cell Junction Proteins in Buccal Mucosa Cells from ACM Gene Carriers Opportunities to characterize molecular pathology in myocardial samples from gene carriers with no clinical evidence of ACM are obviously limited. We were able to prepare buccal mucosa smears from 12 carriers of the recessive mutation in Naxos disease and from 4 carriers of other disease alleles including those with dominant mutations in PKP2 (n=1), DSP (n=2) and DSC2 (n=1) (Group 2; total n=16). None of these subjects exhibited clinical features of ACM although some of the Naxos disease carriers had curly hair. As shown in Table 1, signal for plakoglobin was depressed in 10 of the 12 Naxos disease gene carriers and in 3 of 4 carriers of other mutations. Signal for Cx43 was reduced in 11 of the 12 Naxos carriers and in all 4 carriers of the other mutations. Signal for plakophilin-1 was greatly reduced in the carrier of a dominant PKP2 mutation (n=1) but in none of the other disease gene carriers. Signal for desmoplakin was reduced in carriers of DSC2 (n=1) and DSP mutations (n=2) but not in the other carriers.

Example 1.4

Clinical Correlations with Staining Patterns in ACM Probands and Family Members

All 5 of the ACM patients in Group 1 whose buccal mucosa cells showed apparently normal plakoglobin signal had mutations in PKP2. Three of these patients came to medical attention because the disease had been diagnosed in a family member. Two had mild disease with ventricular ectopy, but no sustained arrhythmias or evidence of structural remodeling. They fulfilled criteria for the diagnosis of ACM mainly on the basis of family history and mutation status. The third patient also came to medical attention because ACM had been diagnosed in her brother. This subject showed ectopy and had an abnormal signal-averaged electrocardiogram but otherwise showed no structural abnormalities and was largely asymptomatic until experiencing an episode of VT storm, 12 years after the diagnosis of ACM was made. The other two ACM patients with PKP2 mutations and normal plakoglobin signal in buccal mucosa cells were Greek individuals both of whom showed marked disease with sustained arrhythmias and right ventricular remodeling.

Family members (Group 3) with apparently normal signal levels included two individuals who were heterozygous for the recessive mutation in JUP that causes Naxos disease. One of these carriers came from a family in which affected individuals exhibited minimal arrhythmias. This particular family member is the daughter of the oldest documented patient with Naxos disease. The other carrier of the Naxos disease mutation whose buccal mucosa cells appeared normal had straight hair and no evidence of heart disease whereas 3 other carriers in the same family (all of whom showed reduced plakoglobin signal) had curly hair but no evidence of heart disease. The third family member with normal plakoglobin and Cx43 signal in buccal mucosa cells was a 14-year old carrier of a disease allele in DSP who showed no evidence of disease.

Example 1.5

Expression of Cell-Cell Junction Proteins in Buccal Mucosa Cells from Patients with Other Heart Diseases We have previously reported that plakoglobin signal at intercalated discs is normal in patients with ischemic heart disease or dilated or hypertrophic cardiomyopathies.[3] This indicates that among this disease spectrum, redistribution of plakoglobin appears to be specific for ACM. By contrast, reduced signal for Cx43 at intercalated discs occurs in various forms of heart disease including both ischemic and non-ischemic cardiomyopathies. Here, we stained buccal mucosa smears from patients with HCM (n=4), DCM (n=2) and ischemic heart disease (n=1) (Group 4). As shown in Table 1, signal for plakoglobin was normal in all of these patients, whereas Cx43 signal was depressed in all cases.

Example 1.6

Studies in Cultured Buccal Mucosa Cells

Figure 3A:
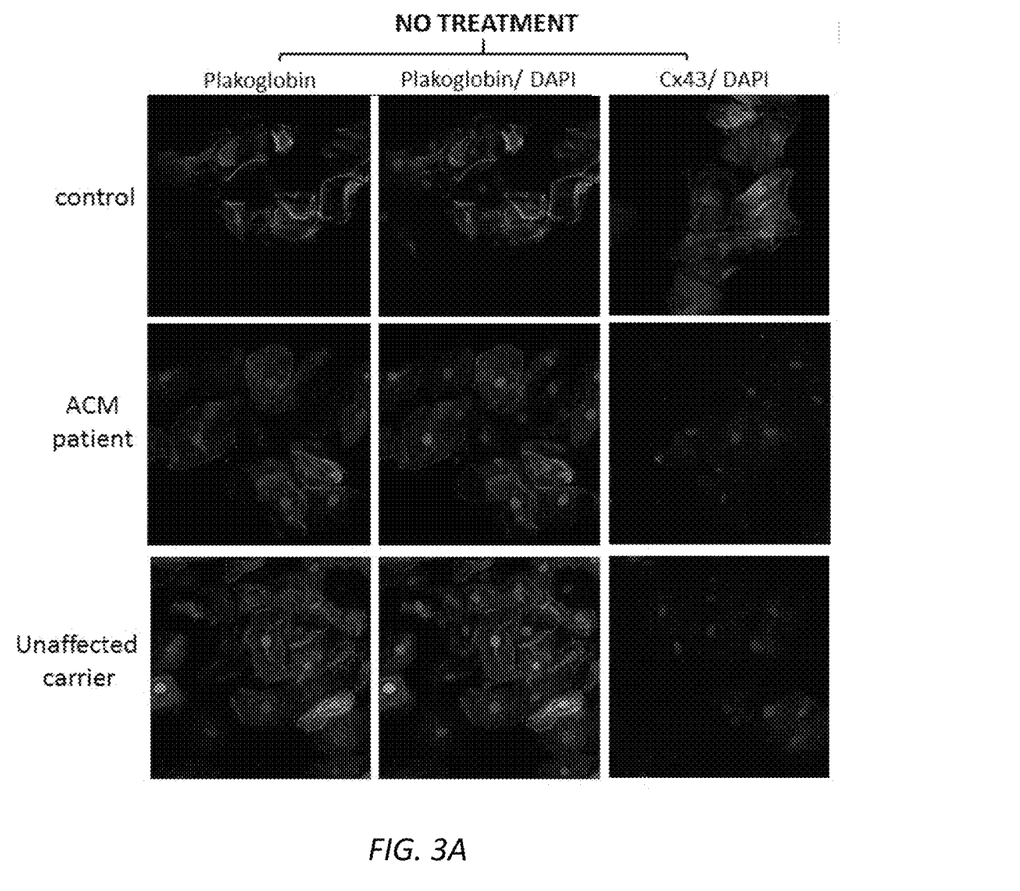
FIGS. 3A-B: Representative images of cultured buccal mucosa cells obtained from a control subject, an ACM patient and a clinically unaffected carrier of a PKP2 mutation, before (A) and after (B) exposure to SB216763. Cultured cells from both the patient and carrier showed loss of junctional signal for plakoglobin, accumulation of nuclear plakoglobin and loss of junctional Cx43. Incubation with SB216763 for 24 hours normalized plakoglobin and Cx43 signal distributions. Cell nuclei (blue) are stained with DAPI.
Figure 3B:
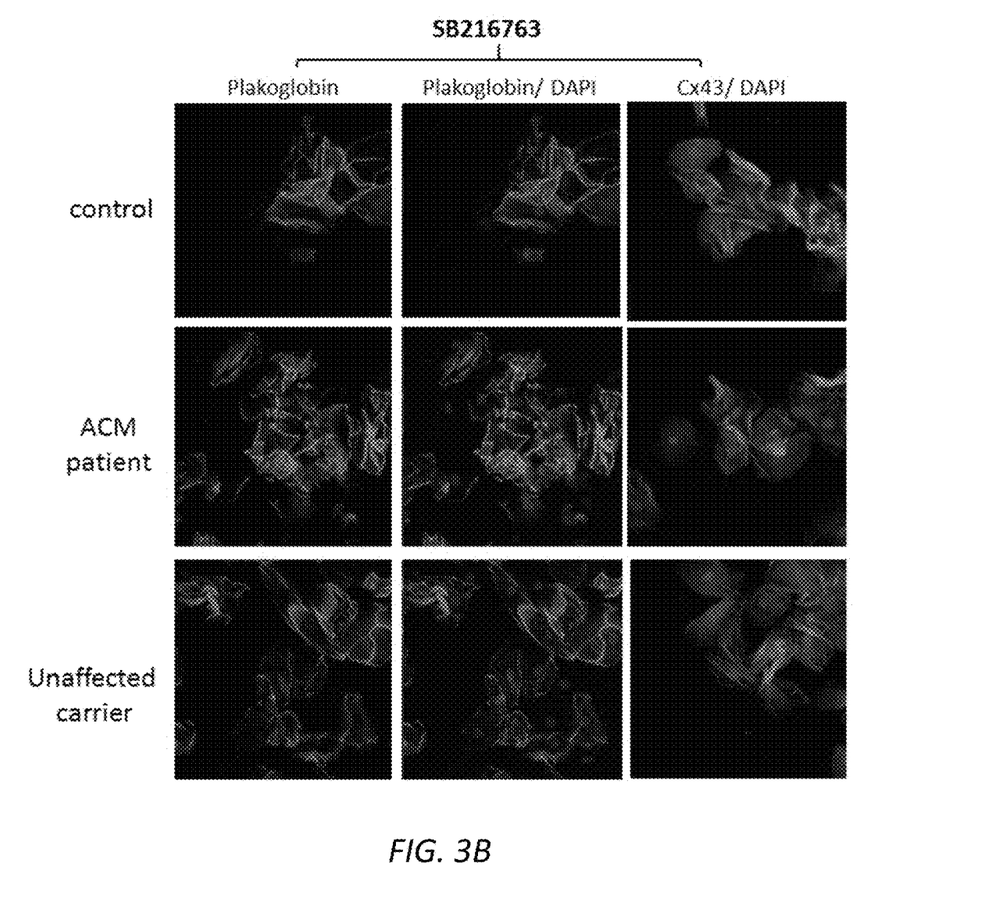

We obtained sufficient material from 6 ACM patients and 2 gene carriers to establish buccal mucosa cell cultures. Cultured cells from all patients and unaffected gene carriers showed loss of junctional signal for plakoglobin and Cx43 while plakoglobin signal accumulated in cell nuclei. In both patients and gene carriers, incubation of cultured cells with SB216763 for 24 hours normalized plakoglobin and Cx43 signal distributions. Representative images are shown in FIGS. 3A-B.

REFERENCES

1. Basso C, Corrado D, Marcus F I, Nava A, Thiene G. Arrhythmogenic right ventricular cardiomyopathy. Lancet. 2009; 373(9671):1289-1300.
2. Marcus F I, Edson S, Towbin J A. Genetics of arrhythmogenic right ventricular cardiomyopathy: a practical guide for physicians. J Am Coll Cardiol. 2013; 61(19): 1945-1948.
3. Asimaki A, Tandri H, Huang H, et al.: A new diagnostic test for arrhythmogenic right ventricular cardiomyopathy. N Eng J Med. 2009; 360(11):1075-1084.
4. Noorman M, Hakim S, Kessler E, et al. Remodeling of the cardiac sodium channel, connexin43 and plakoglobin at the intercalated disk in patients with arrhythmogenic cardiomyopathy. Heart Rhythm. 2013; 10(3):412-419.
5. Fidler L M, Wilson G J, Liu F, et al. Abnormal connexin43 in arrhythmogenic right ventricular cardiomyopathy caused by plakophilin-2 mutations. J Cell Mol Med. 2009; 13(10):4219-4228.
6. Garcia-Gras E, Lombardi R, Giocondo M J, et al. Suppression of canonical Wnt/beta-catenin signaling by nuclear plakoglobin recapitulates phenotype of arrhythmogenic right ventricular cardiomyopathy. J Clin Invest. 2006; 116(7):2012-2021.
7. Kaplan S R, Gard J J, Protonotarios N, et al. Remodeling of myocyte gap junctions in arrhythmogenic right ventricular cardiomyopathy due to a deletion in plakoglobin (Naxos disease). Heart Rhythm. 2004; 1(1):3-11.
8. Asimaki A, Kapoor S, Plovie E, et al. Identification of a new modulator of the intercalated disc in a zebrafish model of arrhythmogenic cardiomyopathy. Sci Transl Med. 2014; 6:240ra74.
9. Kim C, Wong J, Wen J, et al. Studying arrhythmogenic right ventricular dysplasia with patient-specific iPSCs. Nature. 2013; 494(7435):105-110.

10. Caspi O, Huber I, Gepstein A, et al. Modeling of arrhythmogenic right ventricular cardiomyopathy with human induced pluripotent stem cells. Circ Cardiovasc Genet. 2013; 6(6):557-568.
11. Marcus F I, McKenna W J, Sherrill D, et al. Diagnosis of arrhythmogenic right ventricular cardiomyopathy/dysplasia: proposed modification of the task force criteria. Circulation. 2010; 121(13):1533-1541.
arrhythmogenic right ventricular cardiomyopathy with palmoplantar keratoderma and woolly hair (Naxos disease). Lancet. 2000; 355(9221):2119-2124.
13. Presland E B, Dale B A. Epithelial structural proteins of the skin and oral cavity: function in health and disease. Crit Rev Oral Biol Med. 2000; 11(4):383-408.
14. Wong L S, Huzen J, de Boer R A, van Gilst W H, van Veldhuisen D J, van der Harst P. Telomere length of circulating leukocyte subpopulations and buccal cells in patients with ischemic heart failure and their offspring. PLoS One. 2011; 6(8):e23118.
15. Shah S A, Clyne C A, Henyan N, et al. Impact of magnesium sulfate on serum magnesium concentrations and intracellular electrolyte concentrations among patients undergoing radio frequency catheter ablation. Conn Med. 2008; 72(5):261-265.
16. Frank D K, Szymkowiak B, Hughes C A. Connexin expression and gap junctional intercellular communication in human squamous cell carcinoma of the head and neck. Otolaryngol Head Neck Surg. 2006; 135(5):736-743.
17. Brockmeyer P, Jung K, Perske C, Schliephake H, Hemmerlein B. Membrane connexin 43 acts as an independent prognostic marker in oral squamous cell carcinoma. Int J Oncol. 2014; 45(1):273-281.
18. Hartzfeld M. Plakophilins: multifunctional proteins or just regulators of desmosomal adhesion? Biochim Biophys Acta. 2007; 1773(1):69-77.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:
1. A method comprising:
  obtaining a sample comprising buccal cells from the subject; and
  detecting one or both of the level or localization of one or more desmosomal or gap junction proteins selected from the group consisting of plakoglobin, plakophilin 1, desmoplakin, and Cx43 in the subject sample.
2. A method of diagnosing arrhythmogenic cardiomyopathy (ACM) in a subject, the method comprising:
  obtaining a sample comprising buccal cells from the subject;
  detecting the level or localization of one or more desmosomal or gap junction proteins selected from the group consisting of plakoglobin, plakophilin 1, desmoplakin, and Cx43 in the subject sample;
  comparing the level or localization of the one or more cardiac intercalated disk or desmosomal proteins in the subject sample to a reference level or localization; and
  diagnosing ACM in the subject when the level in the subject sample is below the reference level, or when the localization differs from the reference localization.
3. The method of claim 2, where the reference level is a level in a subject who does not have ACM.
4. The method of claim 2, wherein the reference localization is localization in a subject who does not have ACM, optionally localization to cellular junctions.
5. The method of claim 1, wherein the buccal cells were obtained by rubbing the inside of the cheek of the subject with a swab, spatula, or scraper.
6. The method of claim 1, comprising applying the buccal cells onto a surface; optionally fixing the cells; and contacting the cells with an antibody or antigen-binding fragment thereof that binds to a desmosomal or gap junction protein.
7. The method of claim 1, comprising detecting the level and/or localization of plakoglobin;
  plakophilin1;
  desmoplakin;
  Cx43;
  plakoglobin and plakophilin1;
  plakophilin1 and desmoplakin;
  plakoglobin and desmoplakin;
  plakophilin1 and Cx43;
  plakoglobin and Cx43;
  desmoplakin and Cx43;
  plakoglobin, plakophilin 1, and Cx43;
  plakoglobin, desmoplakin, and Cx43;
  plakoglobin, plakophilin1, and desmoplakin;
  plakophilin 1, desmoplakin, and Cx43; or
  plakoglobin, plakophilin 1, desmoplakin, and Cx43.
8. The method of claim 1, comprising detecting the level and/or localization of plakoglobin and Cx43.
9. The method of claim 1, comprising contacting the subject sample with antibodies to:
  plakoglobin;
  plakophilin1;
  desmoplakin;
  Cx43;
  plakoglobin and plakophilin1;
  plakophilin1 and desmoplakin;
  plakoglobin and desmoplakin;
  plakophilin1 and Cx43;
  plakoglobin and Cx43;
  desmoplakin and Cx43;
  plakoglobin, plakophilin 1, and Cx43;
  plakoglobin, desmoplakin, and Cx43;
  plakoglobin, plakophilin1, and desmoplakin;
  plakophilin 1, desmoplakin, and Cx43; or
  plakoglobin, plakophilin 1, desmoplakin, and Cx43.
10. The method of claim 1, comprising contacting the subject sample with antibodies to plakoglobin and Cx43.
11. The method of claim 9, wherein the antibodies are directly or indirectly labeled, and the method comprises detecting the labeled antibodies.
12. The method of claim 1, wherein the subject is at least 7 years of age.
13. The method of claim 2, further comprising selecting a subject diagnosed with ACM for treatment.
14. The method of claim 13, further comprising administering the treatment for ACM to a subject diagnosed with ACM.
15. The method of claim 13, wherein the treatment comprises one or more of recommending or advising the subject to avoid strenuous or intense physical activity or exercise; recommending or prescribing or administering one or more Singh Vaughan Williams class II antiarryhthmics

(beta blockers) such as propranolol, esmolol, timolol, metoprolol, or atenolol; recommending or prescribing or administering one or more class III anti-arrhythmics (K-channel blockers) such as amiodarone, sotalol, ibutilide, dofetilide, dronedarone or E-4031; recommending or performing cardiac ablation; or recommending or implanting an implantable cardiac defibrillator (ICD).

* * * * *

UNITED STATES PATENT AND TRADEMARK OFFICE
CERTIFICATE OF CORRECTION

PATENT NO. : 9,995,756 B2
APPLICATION NO. : 15/277609
DATED : June 12, 2018
INVENTOR(S) : Jeffrey E. Saffitz and Angeliki Asimaki Page 1 of 1

It is certified that error appears in the above-identified patent and that said Letters Patent is hereby corrected as shown below:

On the Title Page

Column 1 (Notice), Line 3, after "0 days." delete "days.";

Column 2 (Other Publications), Line 2, delete "Dalai" and insert -- Dalal --;

In the Claims

In Column 20, Line 67, in Claim 15, delete "antiarryhthmics" and insert -- antiarrhythmic --.

Signed and Sealed this
Thirty-first Day of July, 2018

Andrei Iancu
*Director of the United States Patent and Trademark Office*